(12) United States Patent
Parida

(10) Patent No.: US 7,739,052 B2
(45) Date of Patent: Jun. 15, 2010

(54) PATTERN DISCOVERY TECHNIQUES FOR DETERMINING MAXIMAL IRREDUNDANT AND REDUNDANT MOTIFS

(75) Inventor: Laxmi P. Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 1606 days.

(21) Appl. No.: 10/081,834

(22) Filed: Feb. 22, 2002

(65) Prior Publication Data

US 2003/0046010 A1 Mar. 6, 2003

Related U.S. Application Data

(60) Provisional application No. 60/292,241, filed on May 18, 2001.

(51) Int. Cl.
*G01N 33/48* (2006.01)
*G06G 7/48* (2006.01)
*C12Q 1/68* (2006.01)

(52) U.S. Cl. .............................. 702/19; 702/20; 703/11; 435/6

(58) Field of Classification Search ....................... None
See application file for complete search history.

(56) References Cited

U.S. PATENT DOCUMENTS 6,571,230 B1* 5/2003 Parida .......................... 706/48

2008/0294613 A1* 11/2008 Iyer et al. ...................... 707/4

OTHER PUBLICATIONS

Myers et al. Science, vol. 287, pp. 2196-2204, Mar. 24, 2000.*
SODA 2000. The Eleventh ACM-SIAM Symposium on Discrete Algorithms (SODA) was specifically held on Jan. 9-11, 2000. See "SODA 2000 program," printed from the internet at <http://www.siam.org/meetings/da00/> on Jul. 7, 2008.*
Parida et al., "Pattern Discovery on Character Sets and Real-Valued Data: Linear Bound on Irredundant Motifs and and Efficient Polynomial Time Algorithm," Eleventh ACM-SIAM Symposium on Discrete Algorithms (SODA), 2000.
Parida et al., An Approximation Algorithm for Alignment of Multiple Sequences using Motif Discovery, Journal of Combinatorial Optimization 3, 247-275, 1999.

* cited by examiner

*Primary Examiner*—Shubo (Joe) Zhou
(74) *Attorney, Agent, or Firm*—Ryan, Mason & Lewis, LLP

(57) ABSTRACT

Basis motifs are determined from an input sequence though an iterative technique that begins by creating small solid motifs and continues to create larger motifs that include "don't care" characters and that can include flexible portions. The small solid motifs, including don't care characters and flexible portions, are concatenated to create larger motifs. During each iteration, motifs are trimmed to remove redundant motifs and other motifs that do not meet certain criteria. The process is continued until no new motifs are determined. At this point, the basis set of motifs has been determined. The basis motifs are used to construct redundant motifs. The redundant motifs are formed by determining a number of sets for selected basis motifs. From these sets, unique intersection sets are determined. The redundant motifs are determined from the unique intersection sets and the basis motifs. This process continues, by selecting additional basis motifs.

15 Claims, 7 Drawing Sheets

|   | 0 | 1 | 2 | 3 | 4 |
|---|---|---|---|---|---|
| $m_1$ | a | b | c | . | d |
| $m_2$ | a | b | e |   |   |
| $m_3$ | a | d | d | . | d |
| $m_4$ | a | d | . | . | e |
| $m_5$ | a | b | a | . | d |

|   | 0 | 1 | 2 | 3 | 4 |
|---|---|---|---|---|---|
| $m_1$ | a | b | .[2,3] | e | c |
| $m_2$ | a | b | .[1,2] | b | c |
| $m_3$ | a | b | .[1,3] | b | e |
| $m_4$ | a | .[1,3] | c | b |   |

PATTERN DISCOVERY TECHNIQUES FOR DETERMINING MAXIMAL IRREDUNDANT AND REDUNDANT MOTIFS

CROSS REFERENCE TO RELATED APPLICATIONS

This application claims the benefit of U.S. Provisional Application No. 60/292,241, filed May 18, 2001, the disclosure of which is incorporated by reference herein.

FIELD OF THE INVENTION

The present invention relates to pattern discovery and, more particularly, relates to pattern discovery techniques for determining maximal irredundant and redundant motifs.

BACKGROUND OF THE INVENTION

Pattern or motif discovery in data is widely used as a means of understanding large volumes of data such as Deoxyribo-Nucleic Acid (DNA) or protein sequences. There are a variety of currently existing pattern discovery techniques. Many of these techniques discover "rigid" motifs. Some of these techniques have been extended to "flexible" motifs.

A "rigid" motif is a repeating pattern that has the same length in every occurrence in an input sequence of data. The pattern contained in a rigid motif can contain "don't care" characters, which are generally symbolized by dots. A don't care character means that any character can occupy this particular location. For example, given a string s=abcdaXcdabbcd, the rigid motive m=a.cd occurs twice in the data, at positions 1 and 5 in s. A "flexible" motif is a repeating pattern that has a variable number of don't care characters. For instance, in the previous example, a flexible motif occurs three times, at positions 1, 5 and 9. At position 9, there would be two dot characters to represent two gaps instead of one. This flexible motif may be written as m=a.$^{[1,}$ $_{2]}$cd, where the [1,2] indicates that one or two don't care characters are allowed.

Allowing motifs to have a variable number of don't care characters increases the number of discovered motifs but also increases discovery time and algorithm complexity.

Typically, the higher the number of repeating patterns in a sequence, the higher the number of motifs in the data. Motif discovery on such data, such as repeating DNA or protein sequences, is a source of concern because these data exhibit a very high degree of self-similarity (i.e., repeating patterns). The number of rigid motifs could potentially be exponential in the size of the input sequence and, in the case where the input is a sequence of real numbers, there could be an infinite number of motifs (assuming two real numbers are equal if they are within some $\delta$ of each other).

Usually, this problem of a large number of motifs is tackled by pre-processing the input, using heuristics, to remove the repeating or self-similar portions of the input, or by using a "statistical significance" measure. These types of models, therefore, reduce the number of motifs to a more manageable level. However, due to the absence of a good understanding of the domain, there is no consensus over the right model to use. In other words, if the domain is DNA, there may be insufficient information to know whether a statistical significance measure is correct. Consequently, important motifs may be discarded because of the particular statistical significance measure being used. Thus, there is a trend in different fields towards motif discovery that does not use models.

There has been empirical evidence showing that the runtime for "model-less" motif discovery is linear in the output size for rigid motifs. However, none of the currently known algorithms has a proven output-sensitive complexity bound, and the only known complexity bounds are all exponential in the input size n. In other words, current pattern discovery algorithms depend on the size of the input, regardless of the size of the output of discovered patterns. This is important because one input may be the same size as another, yet produce a much smaller output of discovered patterns. With current pattern discovery, pattern discovery for both of these inputs will take approximately the same amount of time.

In order to apply motif discovery techniques to real life situations, one has to deal with the fact that, in many applications, the input is known with a margin of error. Many amino acids in protein sequences, for instance, are easily interchanged by evolution without loss of function. Also, the use of distance matrices in the context of DNA sequences is common. For example, a character a can be viewed as a or b for pattern detection purposes, but ab cannot be viewed as an a. In all these situations, it is possible to view the input as a string of sets of characters instead of just characters. For instance, a sequence of the form baccta can be viewed as b{a,b}cct{a,b}. In some other applications, the input is an array of real numbers, and two distinct real numbers are deemed identical for pattern detection purposes if they are within some given 67 >0 of each other. Conventional motif discovery algorithms deal with these situations in an ad hoc manner, with no uniform framework, such that the same algorithm cannot tackle all the scenarios described above.

Thus, what is needed are techniques that overcome the following problems: (1) the problem of flexible and rigid pattern discovery within reasonable complexity and time; (2) the problem of solely input-sensitive complexity; and (3) the problem of the non-uniform framework for real numbers and sets of strings of characters during pattern discovery.

SUMMARY OF THE INVENTION

The present invention provides techniques for determining maximal motifs. These techniques have an output-sensitive portion and have proven complexity. Additionally, the techniques support pattern discovery for rigid patterns, flexible patterns, real-number patterns, and patterns having sets of characters for each element. Broadly, from an input sequence, a set of basis motifs are determined. Then, using the basis motifs, a set of redundant motifs are determined. The redundant and basis motifs comprise a set of maximal motifs associated with and defined by the input sequence.

In one aspect of the invention, basis motifs are determined through a technique that begins by creating small solid motifs and continues from there to create larger motifs that include "don't care" characters and that can include flexible portions. A solid motif is a rigid motif without "don't care" characters. A basis motif is an irredundant, maximal motif. The small solid motifs are concatenated to create larger motifs, and these larger motif can include don't care characters and flexible portions. This technique can be iterative. During each iteration, motifs are trimmed to remove redundant motifs and other motifs that do not meet certain criteria. If iterated, the process may be continued until no new motifs are determined. At this point, the basis set of motifs has been determined.

In a second aspect of the invention, the basis motifs are used to construct the redundant motifs. The redundant motifs are formed by determining a number of subsets made of selected basis motifs. From these subsets of basis motifs, unique intersection sets are determined. The redundant motifs are determined from the unique intersection sets and motif sets created from the subsets of basis motifs. This process may also be iterative and can continue, by selecting additional basis motifs, until all basis motifs have been selected.

A more complete understanding of the present invention, as well as further features and advantages of the present invention, will be obtained by reference to the following detailed description and drawings.

DETAILED DESCRIPTION OF PREFERRED EMBODIMENTS

The present invention provides techniques to determine maximal motifs from an input sequence. Pattern discovery techniques in accordance with the present invention proceed in basically two phases. In the first phase, a set of maximal irredundant motifs are determined. These irredundant motifs are called "basis motifs" herein. Using the basis motifs, the present invention, in the second phase, determines a set of maximal redundant motifs. The result of both phases is a set of maximal irredundant and redundant motifs. It should be noted that, if desired, only the basis motifs may be determined.

Some major benefits of the present invention are as follows: (1) the complexity and pattern discovery time are low; (2) the complexity and discovery time are bounded; (3) the complexity and discovery time are related to the output for the redundant motif determination, which is phrased as being "output sensitive"; (4) the basis motifs provide a basis from which additional motifs may be determined; and (5) the present invention may be used for a wide variety of input sequences, including sequences containing real numbers or containing sets of characters. Importantly, the complexity of both phases of the present invention is proportional to the sizes of both the input and the output. More precisely, the complexity of both phases of the present invention is bounded by $O((n^5+N)\log n)$, where "$O(\cdot)$" refers to a complexity on the order of the portion enclosed by parenthesis, the N is the size of the output, and the n is the size of the input.

It should be noted that the term motif is primarily used throughout the present description. However, the term pattern is also used and motif and pattern should be considered equivalent and interchangeable.

Figure 1:
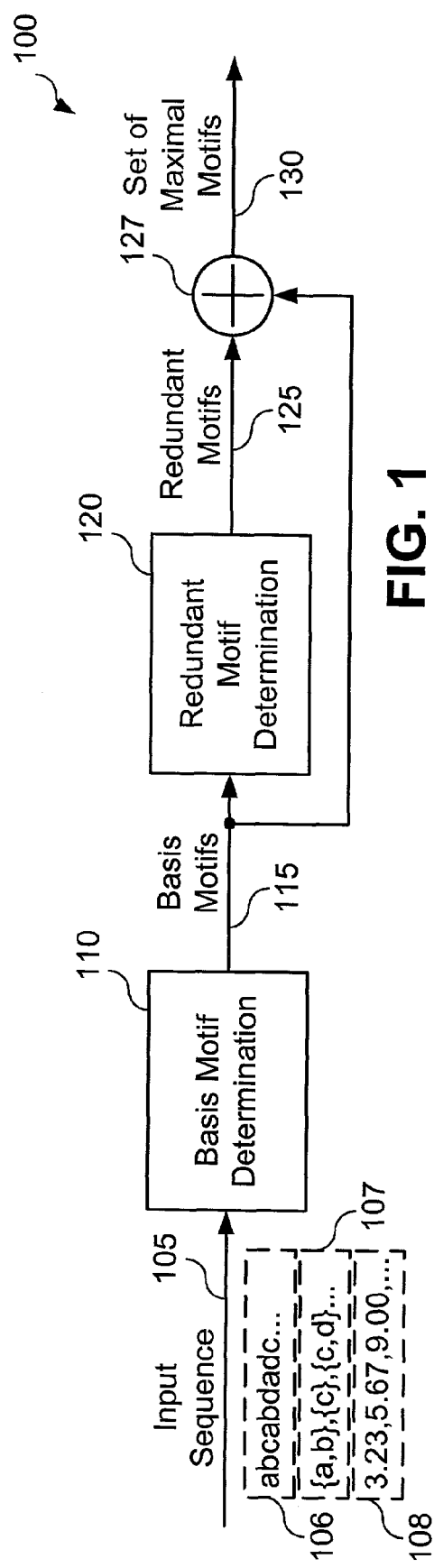
FIG. 1 is a block diagram of a system for determining a set of maximal motifs, in accordance with one embodiment of the present invention.

Referring now to FIG. 1, a system 100 is shown for determining a set of maximal motifs 130 from an input sequence 105. System 100 comprises a basis motif determination operation 110 and a redundant motif determination operation 120. Input sequence 105 is a sequence of elements from an alphabet. Some exemplary input sequences are shown in FIG. 1. Sequence 106 is a series of letters from an alphabet of characters. Generally, the alphabet is a reduced set of characters from the English alphabet. However, any alphabet may be used. Sequence 107 is a series of sets of letters, wherein each letter comes from an alphabet. Sequence 108 is a series of real numbers, for which the alphabet comprises integers. Real numbers may be considered sets of integers. This is described in more detail below.

Figure 3:
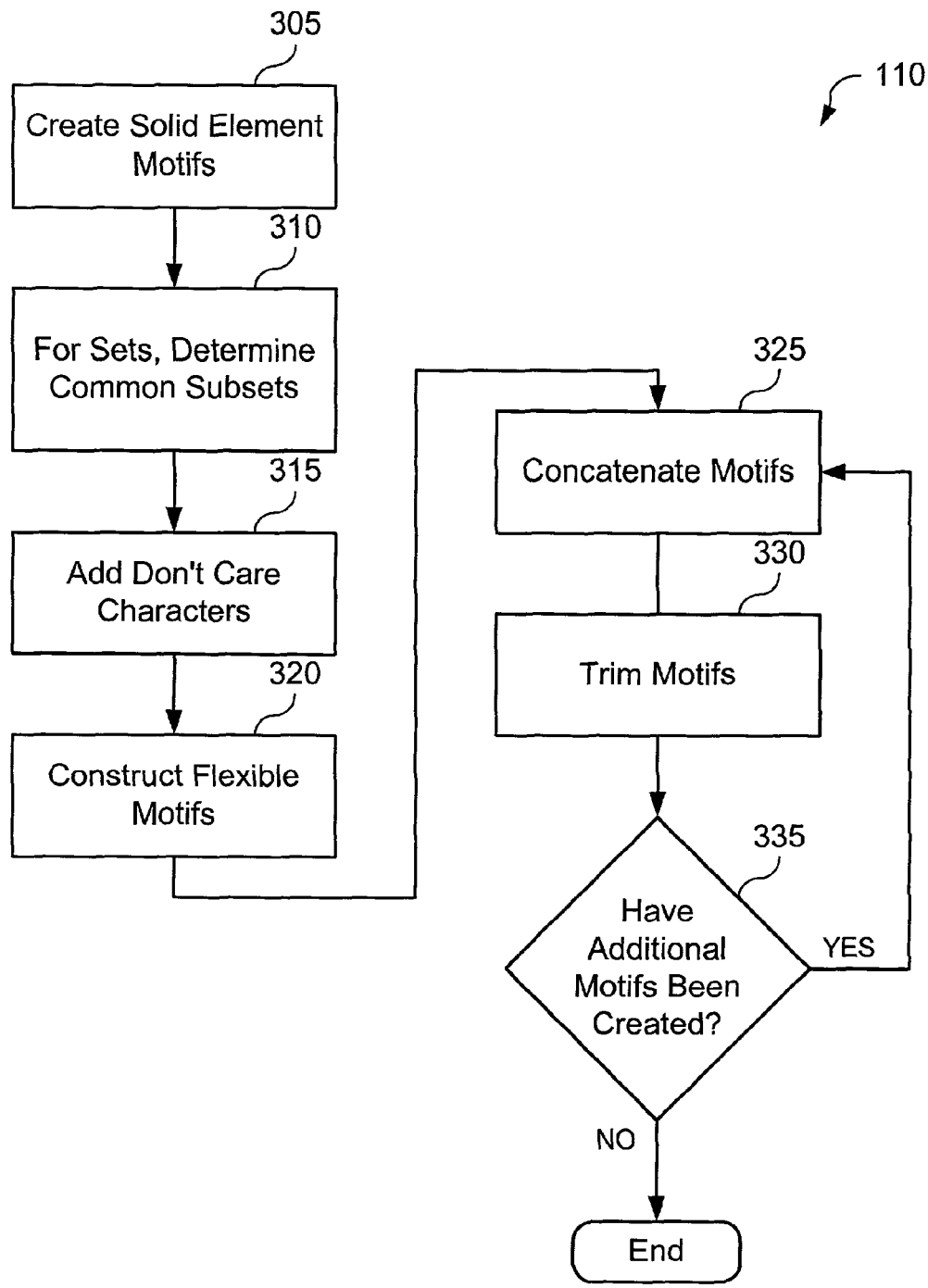
FIG. 3 is a flowchart of a method for creating a basis set of motifs, in accordance with one embodiment of the present invention.

The basis motif determination operation 110 is described in additional detail in reference to FIG. 3. Briefly, the basis motif determination operation 110 accepts a sequence 105 and determines, from the sequence 105, a set of irredundant maximal motifs. These irredundant, maximal motifs are called "basis motifs" herein and are represented by basis motifs 115. Basis motifs 115 are unique motifs that can be used to form other motifs in a space defined by the input sequence 105. Simplistically, "irredundant" means that no basis motif 115 can be formed by a combination of any other basis motifs 115, and "maximal" means that a maximal motif is the largest motif comprising particular elements. These definitions are explained in greater detail below.

Figure 5:
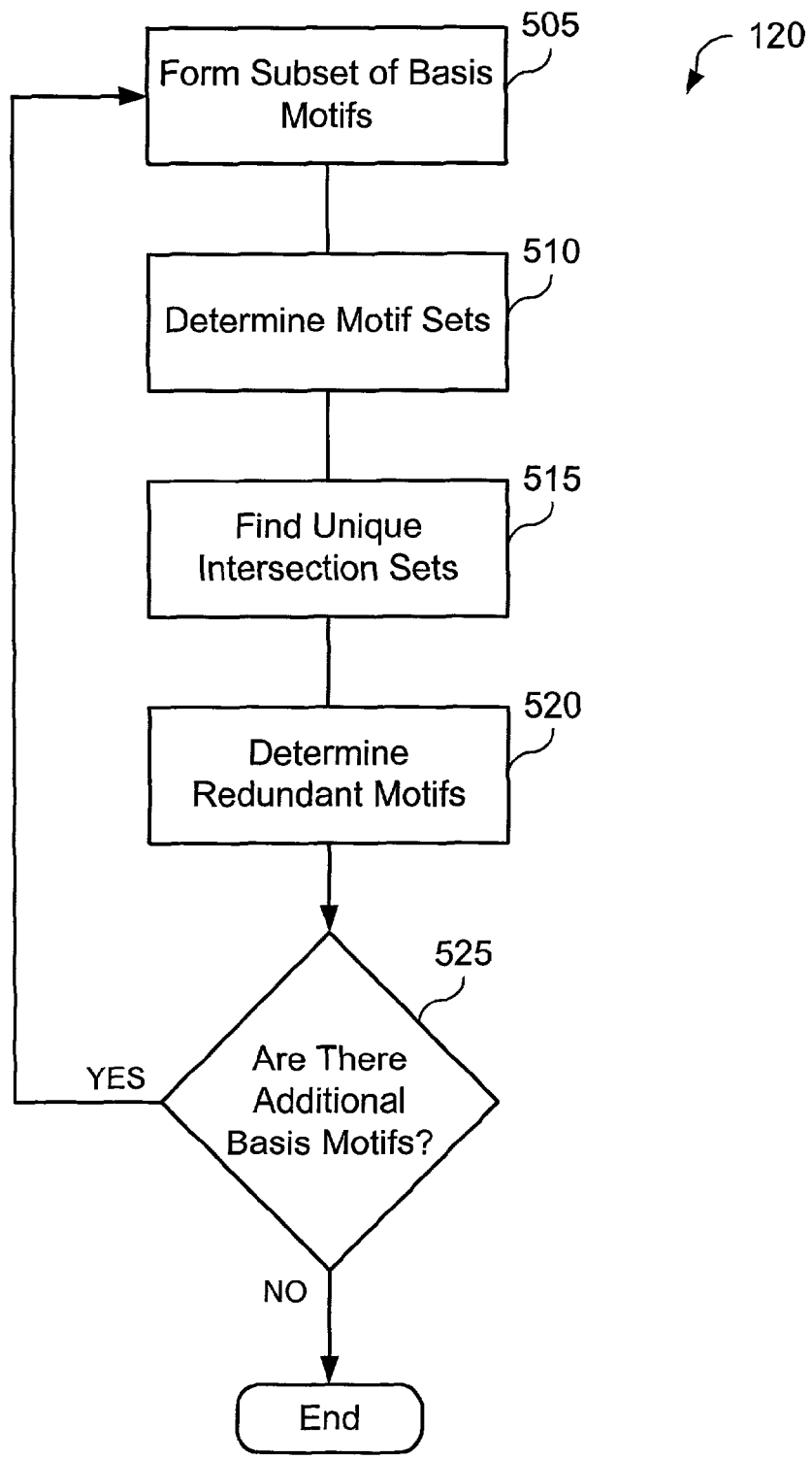
FIG. 5 is a flowchart of a method for creating a redundant set of motifs from a basis set of motifs, in accordance with one embodiment of the present invention.

Redundant motif determination operation 120 is described in more detail in reference to FIG. 5. Briefly, redundant motif determination operation 120 uses the basis motifs 115 to determine a set of redundant motifs 125. Redundant motifs 125 are maximal motifs but may be determined from a combination of basis motifs 115. Redundant motifs 125 and basis motifs 115 are combined in addition module 127 to create a set of maximal motifs 130.

Importantly, both the basis motif determination operation 110 and the redundant motif determination operation 120 have a relatively low complexity compared to current pattern discovery methods. Moreover, system 100 has a running time that is linear in the size of the output (i.e., the set of maximal motifs 130). Thus, system 100 has an output-sensitive complexity bound, and this bound may be proven.

Figure 2:
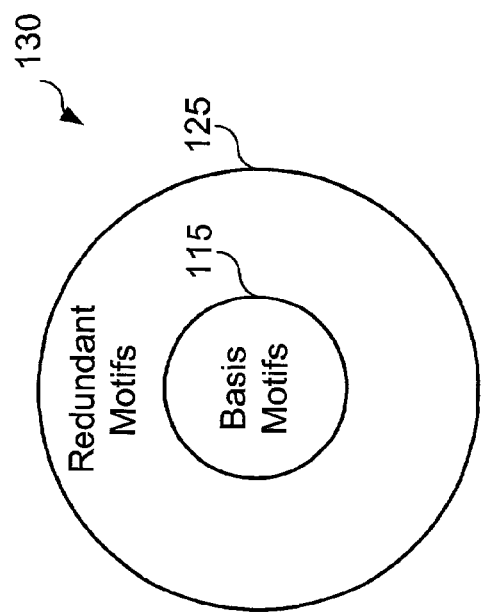
FIG. 2 illustrates a set of maximal motifs.

Referring now to FIG. 2, a simplistic view of a set of maximal motifs 130 is shown. Basis motifs 115 are basically "core" motifs that can be used to determine the redundant motifs 125. The set of maximal motifs 130 is basically a space defined by a particular input sequence. The basis motifs 115 are a set of motifs through which other redundant motifs 125 in the set of maximal motifs 130 may determined. FIG. 2 is discussed herein as an aid to understanding the present invention and should not be construed to be limiting.

Before proceeding with more detailed discussions of basis and redundant motifs and their determination, it is useful to provide some definitions.

Preliminary Definitions

Let s be a sequence of sets of characters from an alphabet $\Sigma$, '.'$\notin \Sigma$. The '.' is called a "don't care" or a dot character and any other element is called solid. Also, $\sigma$ will refer to a singleton character or a set of characters from $\Sigma$. For brevity of notation, a singleton set is not enclosed in curly braces. For example, let $\Sigma=\{A,C,G,T\}$, then $s_1$=ACTGAT and $s_2=\{A,$ T}CG{T,G} are two possible sequences. The $j^{th}$ ($1 \leq j \leq |s|$) element of the sequence is given by s[j]. For instance, in the previous example, $s_2[1]=\{A,T\}$, $s_2[2]=\{C\}$, $s_2[3]=\{G\}$, and $s_2[4]=\{T,G\}$. Also, if x is a sequence, then |x| denotes the length of the sequence, and, if x is a set of elements, then |x| denotes the cardinality of the set. Hence $|s_1|=6$, $|s_2|=4$, $|s_1[1]|=1$, and $|s_2[4]|=2$.

Definition 1: ($e_1 \leq e_2$). The condition ($e_1 \leq e_2$) holds if and only if $e_1$ is a "don't care" character or $e_1 \subseteq e_2$.

The flexibility of a motif is due to the variability in the number of dot characters and flexibility is added by annotating the dot characters.

Definition 2: annotated dot character, ".$^a$". An annotated "." character is written as .$^a$ where a is a set of non-negative integers $\{a_1, a_2, \ldots, a_k\}$ or an interval $a=[a_1, a_u]$ representing all integers between $a_1$ and $a_u$ including $a_1$ and $a_u$.

To avoid clutter, the annotation superscript a will be an integer interval.

Definition 3: rigid and flexible strings. Given a string s, if at least one dot element is annotated, m is called a flexible string; otherwise, m is called rigid.

Definition 4: realization. Let p be a flexible string. A rigid string p' is a realization of p if each annotated dot element .$^a$ is replaced by l dot elements where l∈a.

For example, if p=a.$^{[3,6]}$b.$^{[2,5]}$cde, then p'=a . . . b . . . cde is a realization of p and so is p''=a . . . b . . . cde.

Definition 5: p occurs at l. A rigid string p occurs at position l on s if p[j]≤s[l+j−1] holds for 1≤j≤|p|. A flexible string p occurs at position l in s if there exists a realizations of p' of p that occurs at l.

If p is flexible, then p could possibly occur multiple times at a location on a string s. For example, if s=axbcbc, then p=a.$^{[1,3]}$b occurs twice at position 1 as axbc (i.e., a.bc) and axbcbc (i.e., a . . . bc). This multiplicity of occurrence increases the complexity of an algorithm that discovers flexible motifs over that of an algorithm that discovers rigid motifs.

Definition 6: motif m and location list $£_m$. Given a string s on alphabet Σ and a positive integer k, k≤|s|, a string (flexible or rigid) m is a motif with location list $£_m=(l_1, l_2, \ldots, l_p)$, if m[1]≠'.', m[|m|]≠'.', m occurs at each l∈$£_m$, there exists no l', l'∉$£_m$, and m occurs at l' with p≧k. The requirements for m[1]≠'.' and m[|m|]≠'.' are to ensure that the first and last characters of the motif are solid characters. If don't care characters are allowed at the ends, the motifs can be made arbitrarily long in size without conveying any extra information.

Definition 7: realization of a motif m. Given a motif m on an input string s with a location list $L_m$, and m' a realization of the string m, then m' is a realization of the motif m if and only if there exists some k∈$£_m$ such that m' occurs at k in s.

Notice that because of the present notation of annotating a dot character with an integer interval, instead of a set of integers, not every realization of the flexible motif occurs in the input string. In the remaining description, this stricter definition of motif realization (Definition 7) will be used unless otherwise specified.

Definition 8: ($m_1 \leq m_2$). Given two motifs $m_1$ and $m_2$, with $|m_1| \leq |m_2|$, $m_1 \leq m_2$ holds if, for every realization $m'_1$ of motif $m_1$, there exists a realization $$m'_2$$

of motif $m_2$ such that $$m'_1[j] \leq m'_2[j], 1 \leq j \leq |m_1|.$$

For example, let $m_1$=AB..E, $m_2$=AK..E, and $m_3$=ABC.E.G. Then $m_1 \leq m_3$, and $m_2 \nleq m_3$. The following lemma is straightforward to verify.

Definition 9: ($m_1 = m_2$). Given two motifs $m_1$ and $m_2$ with $|m_1|=|m_2|$, $m_1=m_2$ holds if, for every realization m' of motif $m_1$, there exists a realization $$m'_2$$

of motif $m_2$ such that $$m'_1[j] = m'_2[j], 1 \leq j \leq |m_1|.$$

Lemma 1. If $m_1 \leq m_2$, then $£_{m1} \supseteq £_{m2}$. If $m_1 \leq m_2$ and $m_2 \leq m_3$, then $m_1 \leq m_3$.

Definition 10: sub-motifs of motif m. Given a motif m, let $M[j_1], m[j_2], \ldots m[j_l]$ be the l solid elements in the motif m. Then the sub-motifs of m are given as follows: for every $j_i, j_k$, the sub-motif is obtained by dropping all the elements before (to the left of) $j_i$ and all elements after (to the right of) $j_k$ in m.

Definition 11: maximal motif. Let $p_1, p_2, \ldots, p_k$ be the motifs in a sequence s. Define $p_i[j]$ to be '.', $j>|p_i|$. A motif $p_i$ is maximal in composition if and only if there exists no $p_j$, l≠i with $£_{p_i}=£_{p_j}$, and $p_i \leq p_j$. A motif $p_i$, maximal in composition, is also maximal in length if and only if there exists no motif $p_j$, j≠i, such that $p_i$ is a sub-motif of $p_j$ and $|£_{pi}|=|£_{pj}|$. A maximal motif is maximal both in composition and in length.

Prerequisites

It is quite clear that the number of maximal flexible motifs could be exponential in the size of the input s. It has been shown in that there is a small basis set of motifs of size O(n) for every input of size n. This was shown in Parida, "Some Results on Flexible-Pattern Discovery," Proc. of the Eleventh Symp. on Comp. Pattern Matching, Lecture Notes in Comp. Science, vol. 1848, pages 33-45 (June 2000), the disclosure of which is incorporated herein by reference. The remaining motifs can be computed from this set of motifs. The definition and the statement of the theorem discussed in "Some Results on Flexible-Pattern Discovery" are repeated here.

The notions of redundancy and the basis set will now be defined. Informally speaking, a motif m can be called redundant if m and its location list $£_m$ can be deduced from the other motifs without studying the input string s. This notion is introduced below and it is described below how the redundant motifs and the location lists can be computed from the irredundant motifs.

Definition 12: redundant and irredundant motif. A maximal motif m, with location list $£_m$, is redundant if there exist maximal motifs $m_i$, $1 \leq i \leq p, p \geq 1$, such that $£_m = £_{m_1} \cup £_{m_2} \ldots \cup £_{m_p}$, and $m \leq m_i$ for all i. A maximal motif that is not redundant is called an irredundant motif.

Notice that for a rigid motif p>1 (p in Definition 12), each location list corresponds to exactly one motif, whereas, for a flexible motif, p could have a value of one. For example, let s=axfrgsbapgrftb. Then $m_1$=a.$^{[1,3]}$f.$^{[1,3]}$b, $m_2$=a.$^{[1,3]}$g.$^{[1,3]}$b, and $m_3$=a . . . b with $£_{m_1}=£_{m_2}=£_{m_3}=\{1,8\}$. But $m_3$ is redundant, since $m_3 \leq m_1, m_2$. Also $m_1 \npreceq m_2$ and $m_2 \npreceq m_1$, hence both $m_1$ and $m_2$ are irredundant although $\pounds_{m_1} = \pounds_{m_2}$. This also illustrates the case where one location list corresponds to two distinct flexible motifs (motifs $m_1$ and $m_2$ are distinct if $m_1 = m_2$ does not hold).

Generating operations. The redundant motifs need to be generated from the irredundant ones, if required. The following generating operations are now defined. The binary OR operator $\hat{x}$ is used in the algorithm in the process of motif detection and the AND operator $\oplus$ in the generation of redundant motifs from the basis.

Given an input sequence s, let m, $m_1$, and $m_2$ be motifs. The binary AND operator, $m_1 \oplus m_2$, is defined as follows: $m = m_1 \oplus m_2$, where m is such that $m \leq m_1, m_2$ and there exists no motif m' with $m \leq m'$. For example, if $m_1 = $A.D.$^{[2,4]}$G and $m_2 = $AB...FG, then $m = m_1 \oplus m_2 = $A...$^{[2,4]}$G. The Binary OR operator, $m_1 \times m_2$, is defined as follows: $m = m_1 \hat{x} m_2$, where m is such that $m_1, m_2 \leq m$ and there exists no motif m' with $m' \leq m$. For example, if $m_1 = $A..D..G and $m_2 = $AB...FG, then $m = m_1 \hat{x} m_2 = $AB.D.FG.

Definition 13: basis. Given an input sequence s, let M be the set of all maximal motifs on s. A set of maximal motifs B is called a basis of M if and only if the following hold: (1) for each $m \in B$, m is irredundant with respect to B−{m}; and (2) let G(X) be the set of all the redundant maximal motifs generated by the set of motifs X, then M=G(B).

The following theorem has been proved in "Some Results on Flexible-Pattern Discovery" (which has been previously incorporated by reference), and only the statement of the theorem is given here.

Theorem 1. Let s be a string with n=|s| and let B be a basis or a set of irredundant flexible motifs. Then B is unique and |B|=O(n).

A useful corollary to this theorem is presented below.

Corollary 1. Given an input sequence of length n, let M be a set of motifs, not necessarily maximal, with the following properties: (1) for each p,q∈M, p≠q, let p' be a suffix string of p and p'≠q, unless $|\pounds_p| \neq |\pounds_q|$; and (2) there does not exist p∈M such that $\pounds_p = \cup \pounds_{q_i}$ and $p \leq q_i$ for all i. Then |M|=O(n).

This result is used in the methods of the present invention to bound the number of non-maximal motifs at each iteration of the methods. Next, two problems on sets, the Set Intersection Problem (SIP) and the Set Union Problem (SUP), are described. These are used in the pattern discovery methods discussed below.

The Set Intersection Problem, SIP(n,m,l). Given n sets $S_1, S_2, \ldots, S_n$, on m elements, find all the N distinct sets of the form $S_{i_1} \cap S_{i_2} \cap \ldots S_{i_g}$ with $p \geq 1$. Notice that it is possible that $N=O(2^n)$. An algorithm having a complexity of O(Nlog n+mn) will now be described. This algorithm obtains all the intersection sets.

Given n sets $S_1, S_2, \ldots, S_n$ on m elements, find all the N distinct sets of the form $S_{i_1} \cup S_{i_2} \cup \ldots S_{i_p}$, with $p \leq 1$. Let the elements be numbered 1 . . . m. Construct a binary tree ⊗ using the subroutine CREATE-NODE shown below. Assume a function CREATE-SET(S) which creates S, a subset of $S_1, S_2, \ldots, S_n$ in an appropriate data structure D (for instance, a tree data structure). A query of the form "if a subset S∈D" (i.e., DOES-EXIST(S)) returns a True or False in time O(log n).

Node CREATE-NODE (S; h; l)
{
  (1) New(this-node)

-continued (2) CREATE-SET(S)
  (3) Let S' ={$S_i$ ∈ S|h ∈ $S_i$}
  (4) if ((S' ≥ l) and not DOES-EXIST(S') and (h ≥ 2))
    (5) Left-child = CREATE-NODE(S'; h-1; l)
  (6) Right-child = CREATE-NODE(S; h-1; l)
  (7) return (this-node)
}

For l=2, there is exactly one node the tree ⊗. For l>2, the initial call is CREATE-NODE ($S_1, S_2, \ldots, S_n$; m; l). Clearly, all the unique intersection sets, which are N in number are at the leaf nodes of this tree ⊗. Also, the number of internal nodes can not exceed the number of leaf nodes, N. Thus, the total number of nodes of ⊗ is O(N). The cost of query at each node is O(log n) (line (4) of CREATE-NODE). The size of the input data is O(nm) and each data item is read exactly once in the algorithm (line (3) of CREATE-NODE). Hence, the algorithm takes O(N log n+nm) time. A tree structure created by an SIP algorithm is discussed in reference to FIG. 7.

The Set Union Problem, SUP(n,m). Given n sets $S_1, S_2, \ldots, S_n$ on m elements each, find all the sets $S_i$ such that $S_i = S_{i_1} \cup S_{i_2} \cup \ldots \cup S_{i_p}, i \neq i_j, 1 \leq j \leq p$. An algorithm is now presented that solves this problem in time $O(n^2m)$.

For each set $S_i$, one first obtains the following sets $S_j, j \neq i$, j=1 . . . n, such that $S_j \subset S_i$. This can be done in O(nm) time (for each i). Next, check if $\cup_j S_j = S_i$. Again, this can be done in O(nm) time. Hence, the total time taken is $O(n^2m)$.

Pattern Discovery

The techniques of the present invention can be described as follows. One technique begins by computing solid character patterns and then successively grows them by concatenating with other patterns until patterns cannot be grown any further. Additionally, during the growing process, don't care characters and flexible portions may be added. Unfortunately, the number of patterns at each step grows very rapidly. This problem is ameliorated by first computing only the basis set. This is done by trimming the number of growing patterns at each step and using Theorem 1 to bound their number by O(n). Thus in time $O(n^5 \log n)$, the basis can be detected. Note that this is proportional to only the input. In the next step, the remaining motifs from the basis are computed in time "proportional" to their number.

Computing the Basis (Irredundant) Motifs

The input parameters are: (1) the string, s, (2) the minimum number of times a pattern must appear, k, (3) the flexibility of the dot characters, Δ. Recall that each element of s is a character or a set of characters from the alphabet Σ or even real numbers. If the input is a sequence of real numbers, this problem can be mapped onto an instance of a pattern discovery problem on strings of sets of characters. This is discussed in Parida et al., "Pattern Discovery on Character Sets and Real-Valued Data: Linear Bound on Irredundant Motifs and an Efficient Polynomial Time Algorithm," Eleventh ACM-SIAM Symposium on Discrete Algorithms (SODA), 297-308 (2000), the disclosure of which is incorporated herein by reference. Thus the treatment discussed herein also extends to flexible patterns on real number sequences. The flexibility property has the following interpretation: given a flexibility of Δ, accept dot character annotations of the following form [$a_1, a_2$], where $(a_2 - a_1) \leq \Delta$. For the rest of the description, assume that the alphabet size is |Σ|=O(1).

The following notation is used. Given a motif m (not necessarily maximal), F(m) denotes the first element of m and E(m) denotes the last element of m. Note that F(m)≠'.' and E(m)≠'.'. The location list £'$_m$={(i,j)|m' is the realization of m that occurs at i and ends at j}. Note that the location list £$_m$={i|(i,-)∈£$_m$}.

Turning now to FIG. 3, a method 110 is shown for determining basis motifs from an input sequence. Method 110 is used by a system, such as system 100 of FIG. 1, to determine basis motifs. As discussed above, the input sequence, from which method 110 creates basis motifs, may be real numbers, a DNA sequence, a protein sequence, encrypted files, or any other sequence having an alphabet.

Method 110 begins in step 305, where solid element motifs are created. A solid element motif comprises one or more solid elements, which could be sets or characters. Generally, two elements are used, but the method 110 may also start with fewer or more elements per solid element motif. Broadly, in step 305, for every σ∈Σ, construct m=σ and $$£'_m = \{(i, i) \mid s[i] = \sigma\}.$$

F(m)=E(m)=σ. This step takes O(n) time.

Step 310 is optional and is only required while dealing with strings on sets of characters. In step 310, for sets of characters, common sets are determined. For example if m$_1$={b,c,d} and m$_2$={b,c,e}, step 310 checks to see if m={b,c} exists. Note that £$_m$=£$_{m_1}$∪£$_{m_2}$, while the characters in m are the intersection of the sets of characters in m$_1$ and m$_2$. This problem can be solved using the Set Intersection Problem, SIP (|Σ|,k,2). Assuming |Σ|=O(1), this step takes O(n$^2$) time.

In step 315, don't care characters are added to the solid character motifs to create rigid motifs. For instance, an input sequence could be abced and a solid character motif determined in step 305 might be ab. In step 310, the rigid motif that results after adding a don't care character, to the solid character motif ab is a.c. Note that the rigid motif a.c is a pattern in the input sequence.

Step 315 is stated in more mathematical terms as follows. Let m=m$_{1d2}$ denote the string obtained by concatenating the elements m$_1$ followed by d '.' characters followed by the element m$_2$. For d=0...n, construct the motif m=m$_{idj}$ and the location list $$£'_{m_{idj}} = \{(x, x+d) \mid (x, x) \in £'_{mi}, (x+d, x+d) \in £'_{mj}\}$$

with F(m) = F(m$_i$) and E(m) = E(m$_j$).

This takes O(n$^2$) time, and the number of motifs at this step is O(n).

In the case of flexible motifs, step 320 is performed. In this step, flexible motifs are constructed in the following manner. Construct sets of motifs P such that for all m$_i$,m$_j$∈P, F(m)=F (m$_i$) and E(m$_i$)=E(m$_j$). For each such set P, for l=0...n-Δ, m=m$_i$.$^{[l,l+Δ]}$m$_j$, $$£'_m = \bigcup_{k=1}^{k+l+\Delta} £_{m_{ilj}}$$

and F(m)=F(m$_i$), E(m)=E(m$_j$). This takes O(n$^2$) time and the number of motifs at this step is O(n).

In step 325, concatenation is performed on the motifs created in previous steps. This forms larger motifs. Basically, motifs are concatenated when a "junction" element of a first motif is the same as a "junction" element of a second motif. For instance, if the last element of a first motif is the same as the first element of a second motif, the motifs can be concatenated. This will also hold if each element of a motif is a set of characters. It should be noted that the alternative, i.e., if the first element of a first motif is the same as the last element of a second motif, also means that the two motifs may be concatenated.

In mathematical terms, step 325 is described as follows. Consider every pair of motifs m$_1$ and m$_2$ with E(m$_1$)≦F(m$_2$) or F(m$_1$)≦E(m$_2$). Let l=|m$_1$|. Define as follows:

$$\text{If } E(m_1) \le F(m_2) \text{ then } m[i] = \begin{cases} m_1[i] & i \le l \\ m_2[i - l + 1] & i > l \end{cases}.$$

$$\text{If } F(m_1) \le E(m_2) \text{ then } m[i] = \begin{cases} m_1[i] & i < l \\ m_2[i - l + 1] & i \ge l \end{cases}.$$

For character motifs, which means that each motif is a string of single characters, the formula E(m$_1$)≦F(m$_2$) is actually E(m$_1$)=F(m$_2$). The two cases above are general enough to include sets of characters.

In step 330, trimming is performed on motifs created until this point. This is the pruning step. There are several kinds of pruning performed: (1) where all suffix motifs are removed; (2) where all the "redundant" motifs are removed; and (3) where all motifs that occur less than k times are removed. For the first pruning, every location list is offset to zero and the offset location lists are checked for identity. If identity is found, the location lists with the identity are augmented. An example of this is as follows. If the motif a.b has a location list of £$_{a.b}$={1, 7, 15}, and also the motif bb has a location list of £$_{bb}$={2, 8, 16}, then both of these motifs will have a location list of £={0, 6, 14} when their respective location lists are offset to zero. Essentially, this means that the motif bb is a suffix for the motif a.b. The two motifs are augmented by creating a new motif of abb that has a location list of £$_{abb}$={1, 7, 15}. Removing the suffix motifs ensures that motifs have maximal distance.

The pruning where all the "redundant" motifs are removed will now be described. Let L denote all the location lists of the motifs constructed in previous steps. Using the Set Union Problem, SUP(|L|,n), remove all the motifs whose location list is exactly the union of some other location lists. If £$_m$=∪£$_{m_i}$ remove m and update each m$_i$ as m$_i$=m$_i$⁻m and if |m|>|m$_{i|, E(mi)}$=E(m). For example, if m$_1$=a.b, m$_2$=a..c, and m=a...d with L$_m$=L$_{m_1}$∪L$_{m_2}$ then m$_1$ is updated as m$_1$=a.b.d and m$_2$ is updated as m$_2$=a..cd.

The pruning where all motifs that occur less than k times are removed is self-explanatory. Step 330 takes O(n$^3$) time and the number of motifs at this step is O(n).

In step 335, it is determined if any additional motifs have been created from the previous steps. If not (step 335=NO), the method ends. If one or more additional motifs were created (step 335=YES), then the method continues in step 325. The number of iterations is on the order of log J where J is the length of the longest motif in s. Since J is bounded by n, method 110 takes O(n$^4$ log n) to detect the basis for rigid motifs and O(n$^5$ log n) in the case of flexible motifs. It should be noted that the techniques presented herein for determining basis motifs are not output-sensitive, but are efficient.

Figure 4:
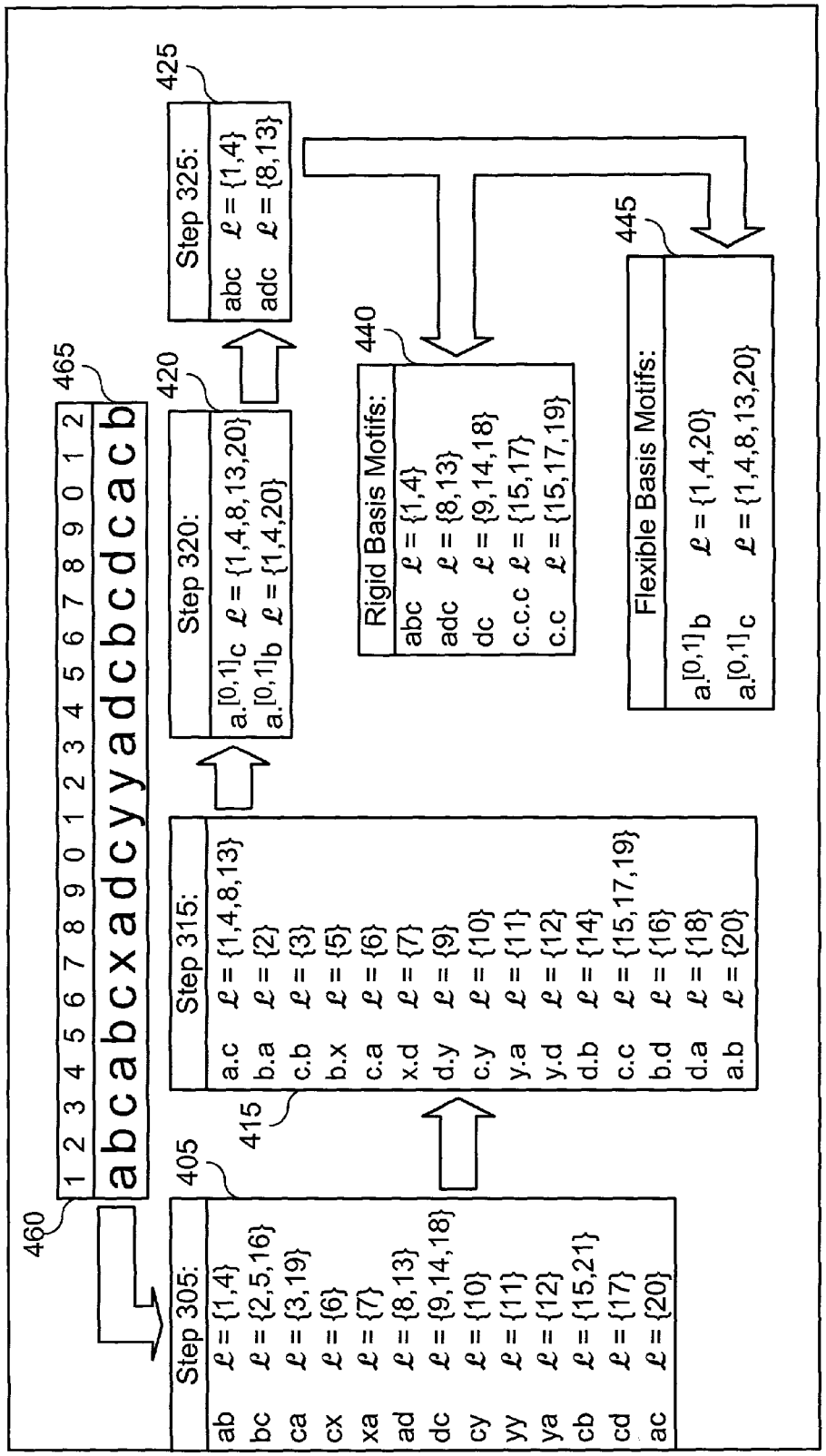
FIG. 4 illustrates an example sequence input, some exemplary partial results of steps in the method of FIG. 3, and resultant basis motifs for the example sequence input.

Referring now to FIG. 4, an example is shown that applies method 110 to a sequence 465 of data. The example of FIG. 4 is used to help explain method 110. Sequence 465 is an exemplary sequence of characters, where the sequence has the alphabet Σ={a,b,c,d,x,y}. Reference 460 is used to help identify locations in sequence 465. For the sake of brevity, all results for each step of method 110 are not shown in FIG. 4. Thus, when "results" are discussed below, the results may not be a complete set of results for the step being discussed. FIG. 4 assumes that k=2 (i.e., motif sets must contain at least two motifs) and d=1 (i.e., there is allowed only one dot character between alphabet characters).

Results 405 are formed during step 305 of FIG. 3, where solid element motifs are created. In this example, two-character solid motifs are formed instead of single-character motifs. It should be noted that, after the pruning step (step 330 of FIG. 3) and because k=2, the only motifs that will remain are ab, bc, ed, and dc. Results 415 are formed during step 315 of FIG. 3, where don't care characters are added. For instance, ab is converted to a.c and bc is converted to b.a. It should be noted that, after the pruning step, the only motifs that will remain are a. c and c.c.

Results 420 are formed during step 320 of FIG. 3, where flexible motifs are created. Two valid flexible motifs are shown in results 420. The motif a.[0,1]b is created from ab (having location list {1,4}) and a.b (having location list {20}). Similarly, the motif a.[0,1]c is created from ac (having location list {20}) and a.c (having location list {1,4,8,13}).

Results 425 are formed during step 325 of FIG. 3, where motifs from previous steps are concatenated. Results 425 are an incomplete list. The motif abc is formed by concatenating ab and bc. Additional examples are the following: a.c could be concatenated with ca to create a.ca; and a.c could be concatenated with c.b to form a.c.b.

If method 110 is executed until completion, rigid basis motifs 440 and flexible basis motifs 445 will result, after multiple pruning steps 330 of FIG. 3.

Techniques for determining basis motifs have now been presented. As previously discussed, the basis motifs are an irredundant set of motifs and are similar to basis vectors. Once the basis motifs have been determined, the redundant motifs may be determined.

Computing Redundant Maximal Patterns

A redundant maximal motif m is of the form $m_1 \oplus m_2 \oplus \ldots \oplus m_p$ for some p and $\pounds_m = \pounds_{m_1} \cup \pounds_{m_2} \cup \ldots \cup \pounds_{m_p}$. It is possible to create redundant maximal motifs through a "brute force" method of combining every possible basis motif. However, an example is given below to show that a straightforward approach of combining (using the operator $\oplus$) compatible motifs does not give the desired time complexity. Two motifs $m_1$ and $m_2$ are compatible, without loss of generality, if $m_1[1] \leq m_2[1]$ and there is i such that $m_1[i] \neq$ '.', $m_2[i] \neq$ '.' and $m_1[i] \leq m_2[i] < i \leq \min(|m_1|,|m_2|)$.

The following example illustrates that a simple combination of motifs is wasteful. Let $m_1$=ab....d, $m_2$=a...cd, $m_3$=a.e..d, $m_4$=a..f.d, with $\pounds_{m_1}$={10,20}, $\pounds_{m_2}$={30,40}, $\pounds_{m_3}$={20,40}, $\pounds_{m_4}$={10,30}. Then $\pounds_{m_5}$={$\pounds_{m_1} \cup \pounds_{m_2} \cup \pounds_{m_3} \cup \pounds_{m_4}$} $\pounds_{m_6}$={$\pounds_{m_2} \cup \pounds_{m_3} \cup \pounds_{m_4}$}, $\pounds_{m_7}$={$\pounds_{m_1} \cup \pounds_{m_3} \cup \pounds_{m_4}$}, $\pounds_{m_8}$={$\pounds_{m_1} \cup \pounds_{m_2} \cup \pounds_{m_4}$}, and $\pounds_{m_9}$={$\pounds_{m_1} \cup \pounds_{m_2} \cup \pounds_{m_3}$} are such that $m_5$=$m_6$=$m_7$=$m_8$=$m_9$=a...d. In other words, the motif $m_5$ is constructed at least four more times than required.

The following is an output-sensitive algorithm to compute all the redundant motifs. Referring now to FIG. 5, a method 120 is shown for determining maximal redundant motifs from basis motifs. Method 120 would be performed by a system such as system 100. Note that method 120 is optional, as the redundant motifs do not have to be determined. Simplistically, method 120 may be explained as follows. The set of basis motifs is split into subsets, each subset containing motifs that have the same first starting element. The motifs in a subset are aligned and placed into a table. Rows of the table are basis motifs and columns of the table are elements in the basis motifs. The term "elements" includes don't care characters, flexible don't care portions, and sets. If a column of the aligned motifs has the same solid character in more than one row, the motifs corresponding to the rows having the same solid character are collected into a set. This set will be called a motif set herein, simply to distinguish it from other sets. There will generally be multiple motif sets. The Set Intersection Problem (SIP) is used to determine a number of unique intersection sets from the motif sets. Each motif set corresponds to a maximal redundant motif, as do the unique intersection sets. After method 120 is discussed in more detail, additional examples will be given and discussed.

Method 120 begins in step 505, where a subset of the basis motifs is formed. Given B the set of all the irredundant motifs, construct ⊓, a set of subsets of B, as follows: P∈⊓, if for each motif $m_i, m_j \in P$, without loss of generality, $F(m_i) \leq F(m_j)$ and $m_i \nleq m_j$, and P is the largest such set. For each P∈∈, construct an instance of the Set Intersection Problem (SIP) as follows.

For each P∈∈ do the following. Let $l = \max_{m \in p} |m|$. Construct $\overline{m}[i]$, $2 \leq i \leq l$ as follows. $\overline{m}[i] = \{\sigma \neq$ '.'$|\sigma \leq p[i], p \in P\}$. Note that it is possible that $\overline{m}[i] = \{\}$ for some i. Now construct an instance of SIP(N',M,2) as follows. The M elements on which the motif sets are built is a subset of the basis set and M=|P|. The N' motif sets are constructed as follows (step 510).

$$S_e^j = \{m_i | \overline{m}[j] = e\}$$

for all possible values of j and e and $$|S_e^j| \geq 2.$$

Assuming that Σ=O(1), the number of such motif sets N'=O(n). Recall that n is length of the input string s whose motifs are being discovered. The unique intersection sets are discovered in step 515 through an instance of the SIP(N',M,2). The SIP has been described above, but is further described in reference to FIG. 7. Each $S_e^j$ with $$|S_e^j| \geq 2$$

corresponds to a maximal redundant motif (step 520). Although the same location lists may give distinct flexible motifs, this does not cause any problems since the solid characters of the motifs in P are used. In step 520, the unique intersection sets discovered in step 515 are used to determine additional redundant motifs.

In step 525, it is determined if there are additional basis motifs that have not be part of a previously used subset. Step 525 is similar to step 335 of FIG. 3. If there are additional basis motifs (step 525=YES), then the method continues at step 505. Note that motif sets of size <k are not formed (in this example, k=2 has been used). If there are no additional basis motifs (step 525=NO), then the method ends. At this point, the redundant maximal motifs for the input sequence have been determined.

The union of the solutions to each of the SIP gives all the maximal redundant motifs in time O(N log n). Recall that N is the number of maximal motifs and n is the length of the input sequence. Thus, method 120 is output-sensitive because its complexity and hence computation time depend on the output as well as the input.

Figure 6:
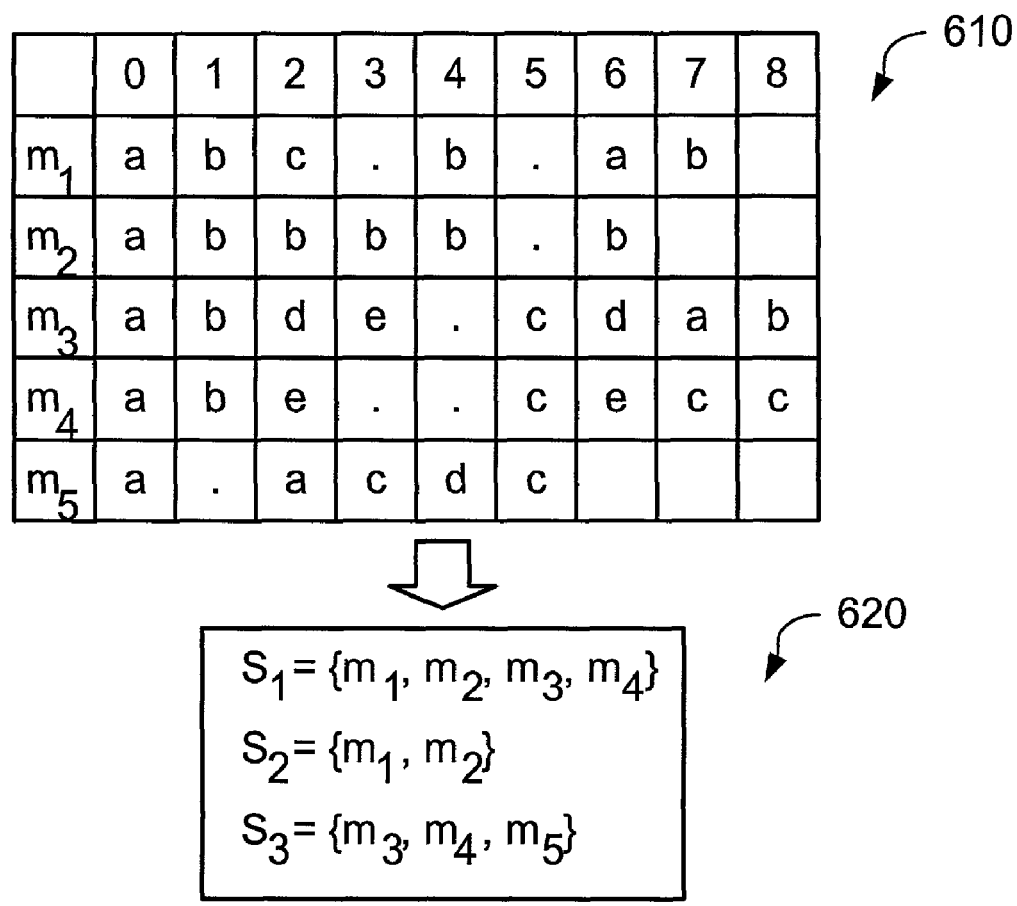
FIG. 6 illustrates an exemplary vector space of basis motifs and resulting sets from the vector space, in accordance with one embodiment of the present invention.

Several examples are now given to help further explain method 120. Referring now to FIG. 6, a subset 610 is shown. Subset 610 comprises five basis motifs, $m_1$, $m_2$, $m_3$, $m_4$, and $m_5$. Each of these basis motifs starts with the same character, a. Each motif is aligned to this first character. Motif sets 620 are created in the following manner. Wherever there is a column containing characters that are the same, the basis motifs corresponding to the equivalent characters are gathered into a set. For instance, to determine motif set $S_1$, note that column 1 contains the character b in four locations. These four locations correspond to the motifs $m_1$, $m_2$, $m_3$, and $m_4$, which form motif set $S_1$. To determine motif set $S_2$, note that column 4 contains the character b in two locations. These two locations correspond to the motifs $m_1$ and $m_2$, which form motif set $S_2$. To determine motif set $S_3$, note that column 4 contains the character c in three locations. These three locations correspond to the motifs $m_3$, $m_4$, and $m_5$, which form motif set $S_3$.

Figures 7, 8, 9:
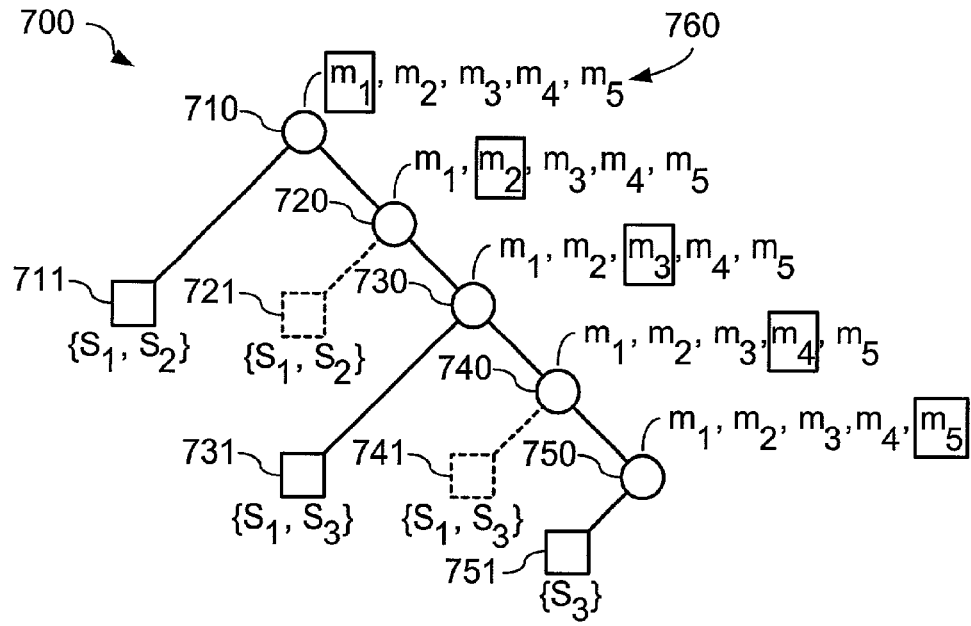
FIG. 7 illustrates an exemplary tree used to determine unique intersections sets from the sets shown in FIG. 6, in accordance with one embodiment of the present invention.
FIGS. 8 and 9 show additional exemplary vector spaces created from basis motifs, in accordance with one embodiment of the present invention.

Now that motif sets have been determined, unique intersection sets are determined. A tree 700 is constructed and shown in FIG. 7. Tree 700 comprises nodes 710, 720, 730, 740, and 750 and "leaves" 711, 721, 731, 741, and 751. Each leaf corresponds to an intersection set, and, consequently, the term "intersection set" will be used herein. At each node, a group 760 of motifs is used to determine intersection sets. This group 760 is the subset 610 of motifs shown in FIG. 6. The group 760 is a set of motifs that can be numbered or assigned to columns arbitrarily from 1 . . . m, where m is the total number of motifs. At each node of the tree, only one motif from a group is considered. In the example of FIG. 7, a box is placed around the motif that is being considered from group 760.

At the root node 710, for instance, one of the motifs in the group 760 is selected and considered. At the next node 720, another of the motifs in the group 760 is selected and considered. This process continues through each node. At each node, a left child group is created from the intersection set of all those motif sets that has the motif being considered (e.g., motif $m_i$), provided this intersection has not already been created. The right child is the parent set minus the motif already considered. This process ensures that the tree can have a depth, measured in nodes, no bigger than m.

Although the motifs may be selected at random, the present example will start with the first motif, $m_1$, end with the last motif, $m_5$, and process the motifs in order. At node 710, for the selected basis motif $m_1$, there is one intersection set 711 of $\{S_1, S_2\}$ (i.e., only sets $S_1$ and $S_2$ contain basis motif $m_1$). At node 720, for the selected basis motif $m_2$, there is an intersection set 721 of $\{S_1, S_2\}$; however, this set is not unique and is discarded. At node 730, for the selected motif $m_3$, there is an intersection set 731 of $\{S_1, S_3\}$. At node 740, for the motif $m_4$, there is an intersection set 741 of $\{S_1, S_3\}$; however, this intersection is not unique and is discarded. The final intersection set 751 is $\{S_3\}$, but this intersection set is also not unique and it does not have a size greater than one. Thus, the unique intersection sets are $\{S_1, S_2\}$ and $\{S_1, S_3\}$.

The redundant motifs are then determined from $S_1$, $S_2$, $S_3$, $\{S_1, S_2\}$, and $\{S_1, S_3\}$ as follows. The intersection of $S_1$ and $S_2$ is $S_1 \cap S_2 = \{m_1, m_2\} = ab..b$, with location list $\pounds = \pounds_{m_1} \cup \pounds_{m_2}$. The intersection of $S_2$ and $S_3$ is $S_1 \cap S_3 = \{m_3, m_4\} = a...c$, with location list $\pounds = \pounds_{m_3} \cup \pounds_{m_4}$. The intersection of the motif set $S_1$ is $S_1 = \{m_1, m_2, m_3, m_4\} = ab$, with location list $\pounds = \pounds_{m_1} \notin \pounds_{m_2} \cup \pounds_{m_3} \cup \pounds_{m_4}$. The intersection of the motif set $S_2$ is $S_2 = \{m_1, m_2\} = ab..b$, but this motif has already been determined. The intersection of the motif set $S_3$ is $S_3 = \{m_3, m_4, m_5\} = a....c$, with location list $\pounds_{m_3} \cup \pounds_{m_4} \cup \pounds_{m_5}$.

As another illustration, a second example involving rigid motifs is shown in FIG. 8. As shown in FIG. 8, let $m_1 = abc.d$, $m_2 = abe$, $m_3 = add.d$, $m_4 = ad..e$, and $m_5 = ab..d$. Here $l = 5$ and $S_b^2 = \{m_1, m_2, m_5\}$, $$S_d^2 = \{m_3, m_4\}, S_d^5 = \{m_1, m_3, m_5\}.$$

Each of the motif sets corresponds to a maximal redundant motif. For example $$S_b^2$$

gives the maximal redundant motif of $m_1 \oplus m_2 \oplus m_5 = ab$ with location list $l_{m_1} \cup L_{m_2} \cup L_{m_5}$, $$S_d^2$$

gives the maximal redundant motif of $m_3 \oplus m_4 = ad$ with location list $L_{m_3} \cup L_{m_4}$, $$S_d^5$$

give $m_1 \oplus m_3 \oplus m_5 = a\ a...d$ with location list $L_{m_1} \cup L_{m_3} \cup L_{m_5}$. The results from SIP give the unique intersection set $\{m_1, m_5\}$ and this corresponds to the motif $m = m_1 \oplus m_5 = ab..d$ with $L_m = L_{m_1} \cup L_{m_5}$.

Consider an example using flexible motifs. This example is shown in FIG. 9. As shown in FIG. 9, let $m_1 = ab.^{[2,3]}ec$, $m_2 = ab.^{[1,2]}bc$, $m_3 = ab.^{[1,3]}be$, and $m_4 = a.^{[1,3]}cb$. Here $l = 5$. The different motif sets are the following:

$$S_b^2 = \{m_1, m_2, m_3\},$$

$$S_b^4 = \{m_2, m_3, m_4\}, S_c^5 = \{m_1, m_2\}.$$

Each of the motif sets corresponds to a maximal redundant motif. The motif set $$S_b^2$$

gives $m_1 \oplus m_2 \oplus m_3 = ab$, with location list $L_{m_2} \cup L_{m_3} \cup L_{m_4}$. The motif set $$S_b^4$$

gives $m_2 \oplus m_3 \oplus m_4 = a.^{[1,3]}.^{[1,2]}b = a.^{[2,5]}b^5$ with location list $L_{m_2} \cup L_{m_3} \cup L_{m_4}$. The motif set $$S_c^5$$

gives $m_1 \oplus m_2 = ab.^{[1,3]}.^{[1,2]}c = ab.^{[2,5]}c$ with location list $L_{m_1} \cup L_{m_2}$. The intersection results from SIP gives $\{m_2, m_3\}$ with $m = m_2 \oplus m_3 = ab.^{[1,3]}b$ and location list $L_{m_2} \cup L_{m_3}$.

Exemplary System

Figure 10:
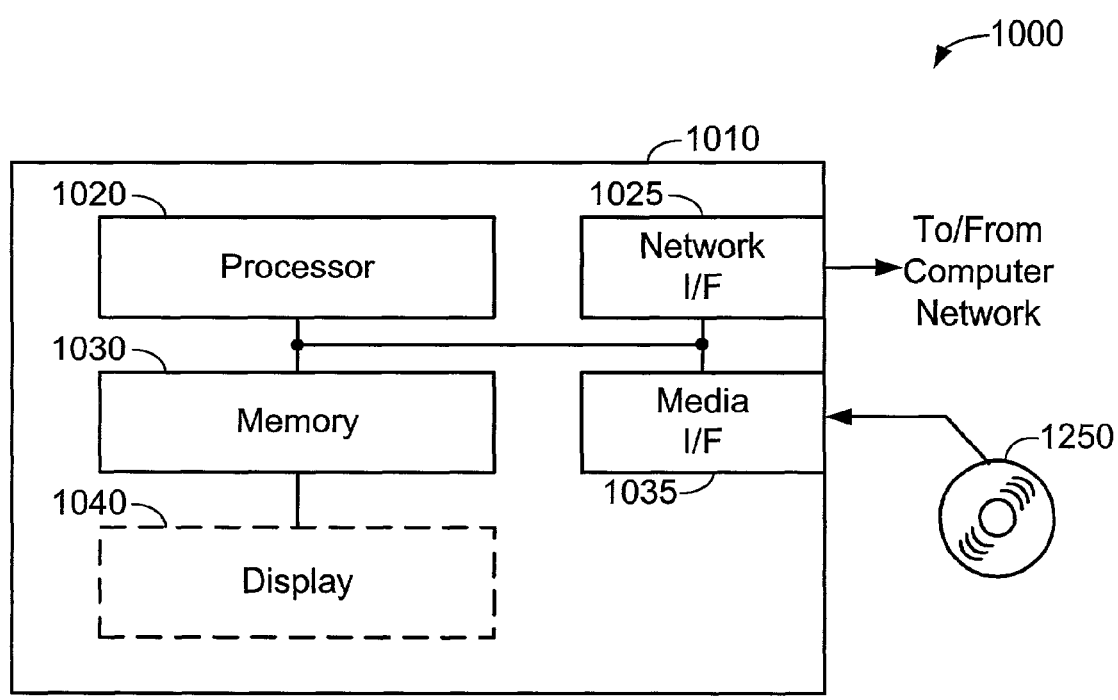
FIG. 10 shows an exemplary system, in accordance with one embodiment of the present invention, suitable for performing the present invention.

Turning now to FIG. 10, a block diagram is shown of a system 1000 for determining irredundant and redundant motifs in accordance with one embodiment of the present invention. It should be understood that system 1200 represents one embodiment for implementing system 100 of FIG. 1. System 1000 comprises a computer system 1010 and a Digital Versatile Disk (DVD) 1050. Computer system 1010 comprises a processor 1020, a memory 1030 and a video display 1040. Computer system 1010 comprises a processor 1020, a network interface 1025, a memory 1030, a media interface 1035, and an optional display 1040. Network interface 1025 allows computer system 1010 to connect to a network, while media interfaces 1035 allows computer system 1035 to interact with media such as a hard drive or DVD 1050.

As is known in the art, the methods and apparatus discussed herein may be distributed as an article of manufacture that itself comprises a computer-readable medium having computer-readable code means embodied thereon. The computer-readable program code means is operable, in conjunction with a computer system such as computer system 1010, to carry out all or some of the steps to perform the methods or create the apparatuses discussed herein. The computer-readable medium may be a recordable medium (e.g., floppy disks, hard drives, optical disks such as DVD 1050, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk, such as DVD 1050.

Memory 1030 configures the processor 1020 to implement the methods, steps, and functions disclosed herein. The memory 1030 could be distributed or local and the processor 1020 could be distributed or singular. The memory 1030 could be implemented as an electrical, magnetic or optical memory, or any combination of these or other types of storage devices. Moreover, the term "memory" should be construed broadly enough to encompass any information able to be read from or written to an address in the addressable space accessed by processor 1010. With this definition, information on a network, accessible through network interface 1025, is still within memory 1030 because the processor 1020 can retrieve the information from the network. It should be noted that each distributed processor that makes up processor 1020 generally contains its own addressable memory space. It should also be noted that some or all of computer system 1010 can be incorporated into an application-specific or general-use integrated circuit.

Optional video display 1040 is any type of video display suitable for interacting with a human user of system 1000. Generally, video display 1040 is a computer monitor or other similar video display.

It is to be understood that the embodiments and variations shown and described herein are merely illustrative of the principles of this invention and that various modifications may be implemented by those skilled in the art without departing from the scope and spirit of the invention.

What is claimed is:

1. A method for pattern discovery on an input sequence comprising a plurality of elements, the method comprising the steps of:

providing a system, wherein said system comprises a memory device, at least one hardware processor device coupled to said memory device, and a software module loadable into said memory device and executable on said at least one hardware processor device;

determining a plurality of first motifs from the input sequence, each first motif comprising at least one element from the input sequence, wherein said determining step is performed by said at least one hardware processor device;

concatenating each of the plurality of first motifs with another of the plurality of first motifs to create a plurality of concatenated motifs, wherein said concatenating step is performed by said at least one hardware processor device;

removing one or more selected motifs, wherein said one or more selected motifs are any of the concatenated motifs and the first motifs, wherein the step of removing comprises removing suffix motifs, wherein each motif in the concatenated motifs and the first motifs has an associated location list, and wherein said removing step is performed by said at least one hardware processor device, and wherein the step of removing suffix motifs comprises the steps of:

offsetting each location list for each of the motifs in the concatenated motifs and the first motifs to zero, wherein said offsetting step is performed by said at least one hardware processor device;

checking each location list for each of the motifs in the concatenated motifs and the first motifs to determine location lists that are the same, wherein said checking step is performed by said at least one hardware processor device; and concatenating motifs that have the same location list to create at least one new motif, wherein said concatenating motifs step is performed by said at least one hardware processor device; and providing at least said at least one new motif as an output, wherein said providing step is performed by said software module executing on said at least one hardware processor.

2. The method of claim 1, further comprising the step of selecting motifs of the concatenated motifs and the first motifs for removal based on at least one predetermined criteria.

3. The method of claim 1, wherein the step of removing comprises removing redundant motifs in the concatenated motifs and the first motifs.

4. The method of claim 3, wherein each motif in the concatenated motifs and the first motifs has an associated location list, and wherein the step of removing redundant motifs comprises the steps of:
- determining any motif whose location list is a union of other location lists associated with motifs in the concatenated motifs and the first motifs; and
- removing any motif whose location list is a union of other location lists associated with motifs in the concatenated motifs and the first motifs.

5. The method of claim 1, wherein the step of removing comprises removing selected motifs in the concatenated motifs and the first motifs if the selected motifs do not occur in the concatenated motifs and the first motifs more than a predetermined number of times.

6. The method of claim 1, further comprising the step of:
- performing the steps of concatenating and removing until no new motifs are generated by said concatenating and removing steps.

7. The method of claim 6, wherein one or more remaining motifs of the concatenated motifs and the first motifs form a basis set of motifs and wherein the method further comprises the steps of:
- determining a plurality of motif sets from a plurality of selected motifs, the selected motifs selected from a plurality of basis motifs, wherein the plurality of selected motifs all begin with a selected element;
- determining unique intersection sets from the plurality of motif sets; and
- determining redundant motifs from the intersection sets and the motif sets.

8. The method of claim 1, wherein:
each first motif is a solid element motif;
the step of determining a plurality of first motifs comprises the steps of:
- determining a plurality of solid element motifs, each solid element motif comprising at least one element from the input sequence; and
- creating a plurality of second motifs by adding at least one don't care element to each of the solid element motifs;

the step of concatenating further comprises the steps of:
- selecting a motif from the solid element and second motifs;
- concatenating the selected motif with another selected motif from the solid element and second motifs; and
- performing the process of selecting and concatenating until each motif from the solid element and second motifs has been concatenated with another motif from the solid element and second motifs;

the method of claim 4 further comprises the steps of:
- trimming the solid element, second, and concatenated motifs; and
- performing the steps of concatenating and trimming until no new motifs are generated by said concatenating and trimming steps.

9. The method of claim 8, further comprising the step of creating flexible motifs from the first motifs.

10. The method of claim 1, further comprising the step of creating flexible motifs from the first motifs.

11. The method of claim 1, wherein each element of the input sequence comprises a character from an alphabet.

12. The method of claim 1, wherein at least one element of the input sequence comprises a set of characters.

13. The method of claim 1, wherein each element of the input sequence comprises a real number.

14. A computer system for pattern discovery on an input sequence comprising a plurality of elements, comprising:
- a memory that stores computer-readable code;
- a processor operatively coupled to the memory, the processor configured to implement the computer-readable code, the computer-readable code configured to:
  - determine a plurality of first motifs from the input sequence, each first motif comprising at least one element from the input sequence;
  - concatenate each of the plurality of first motifs with another of the plurality of first motifs to create a plurality of concatenated motifs; and
  - remove one or more selected motifs, wherein said one or more selected motifs are any of the concatenated motifs and the first motifs, wherein the removal comprises removing suffix motifs, and wherein each motif in the concatenated motifs and the first motifs has an associated location list, and wherein the step of removing suffix motifs comprises the steps of:
    - offsetting each location list for each of the motifs in the concatenated motifs and the first motifs to zero;
    - checking each location list for each of the motifs in the concatenated motifs and the first motifs to determine location lists that are the same; and
    - concatenating motifs that have the same location list to create at least one new motif; and
- provide at least said at least one new motif as an output.

15. An article of manufacture for pattern discovery on an input sequence comprising a plurality of elements, comprising:
- a computer readable storage medium having computer-readable code means embodied thereon, the computer-readable program code means comprising:
- a step to determine a plurality of first motifs from the input sequence, each first motif comprising at least one element from the input sequence;
- a step to concatenate each of the plurality of first motifs with another of the plurality of first motifs to create a plurality of concatenated motifs; and
- a step to remove one or more selected motifs, wherein said one or more selected motifs are any from the concatenated motifs and the first motifs, wherein the step of removing comprises removing suffix motifs, and wherein each motif in the concatenated motifs and the first motifs has an associated location list, and wherein the step of removing suffix motifs comprises the steps of:
  - offsetting each location list for each of the motifs in the concatenated motifs and the first motifs to zero;
  - checking each location list for each of the motifs in the concatenated motifs and the first motifs to determine location lists that are the same; and
  - concatenating motifs that have the same location list to create at least one new motif; and
- a step to provide at least said at least one new motif as an output.

* * * * *